(12) United States Patent
Pelissier et al.

(10) Patent No.: US 8,920,325 B2
(45) Date of Patent: Dec. 30, 2014

(54) HANDHELD ULTRASOUND IMAGING SYSTEMS

(75) Inventors: Laurent Pelissier, North Vancouver (CA); Kris Dickie, Vancouver (CA); Kwun-Keat Chan, Vancouver (CA)

(73) Assignee: Ultrasonix Medical Corporation, British Columbia (CA)

(*) Notice: Subject to any disclaimer, the term of this patent is extended or adjusted under 35 U.S.C. 154(b) by 109 days.

(21) Appl. No.: 13/476,142

(22) Filed: May 21, 2012

(65) Prior Publication Data

US 2012/0232380 A1 Sep. 13, 2012

Related U.S. Application Data

(63) Continuation of application No. 12/188,122, filed on Aug. 7, 2008, now abandoned.

(60) Provisional application No. 60/977,353, filed on Oct. 3, 2007.

(51) Int. Cl.
*A61B 8/00* (2006.01)

(52) U.S. Cl.
CPC .................. *A61B 8/00* (2013.01); *A61B 8/4455* (2013.01); *A61B 8/462* (2013.01); *A61B 8/465* (2013.01)
USPC .......................................... 600/446; 600/443

(58) Field of Classification Search
None
See application file for complete search history.

(56) References Cited

U.S. PATENT DOCUMENTS

| 5,295,485 | A | 3/1994 | Shinomura et al. |
| 5,590,658 | A | 1/1997 | Chiang et al. |
| 5,722,412 | A | 3/1998 | Pflugrath et al. |
| 5,817,024 | A | 10/1998 | Ogle et al. |
| 6,106,472 | A | 8/2000 | Chiang et al. |
| 6,203,498 | B1 | 3/2001 | Bunce et al. |
| 6,251,073 | B1 | 6/2001 | Imran et al. |
| 6,569,102 | B2 | 5/2003 | Imran et al. |
| 6,575,908 | B2 | 6/2003 | Barnes et al. |
| 6,638,226 | B2 | 10/2003 | He et al. |
| 6,837,853 | B2 * | 1/2005 | Marian .................. 600/437 |
| 6,953,433 | B2 | 10/2005 | Kerby et al. |
| 7,115,093 | B2 | 10/2006 | Halmann et al. |
| 7,221,972 | B2 | 5/2007 | Jackson et al. |
| 2004/0138564 | A1 | 7/2004 | Hwang et al. |
| 2004/0147840 | A1 | 7/2004 | Duggirala et al. |
| 2004/0158154 | A1 | 8/2004 | Hanafy et al. |
| 2004/0171935 | A1 * | 9/2004 | Van Creveld et al. ......... 600/437 |
| 2004/0181154 | A1 | 9/2004 | Peterson et al. |
| 2005/0049494 | A1 | 3/2005 | Gritzky et al. |
| 2005/0054927 | A1 | 3/2005 | Love |

(Continued)

FOREIGN PATENT DOCUMENTS

WO  WO2008009044  * 1/2008
WO  WO2009129845  * 10/2009

*Primary Examiner* — Christopher Cook
(74) *Attorney, Agent, or Firm* — Anthony M. Del Zoppo, III; Driggs, Hogg, Daugherty & Del Zoppo Co. LPA

(57) ABSTRACT

A handheld ultrasound device is provided, having a transducer assembly for emitting and receiving sonic signals, a configurable signal processing unit, and a data processor configured to provide configuration data to the signal processing unit. The configuration data defines a beamforming configuration, filtering configuration and envelope detection configuration for an operational mode. The operational mode may be selected by the user or may be determined based on a detected type of the transducer assembly.

20 Claims, 8 Drawing Sheets

(56) References Cited

U.S. PATENT DOCUMENTS

| | | | |
|---|---|---|---|
| 2005/0228281 A1* | 10/2005 | Nefos | 600/446 |
| 2007/0073155 A1 | 3/2007 | Park et al. | |
| 2007/0161904 A1* | 7/2007 | Urbano | 600/459 |
| 2008/0221446 A1* | 9/2008 | Washburn et al. | 600/437 |

* cited by examiner

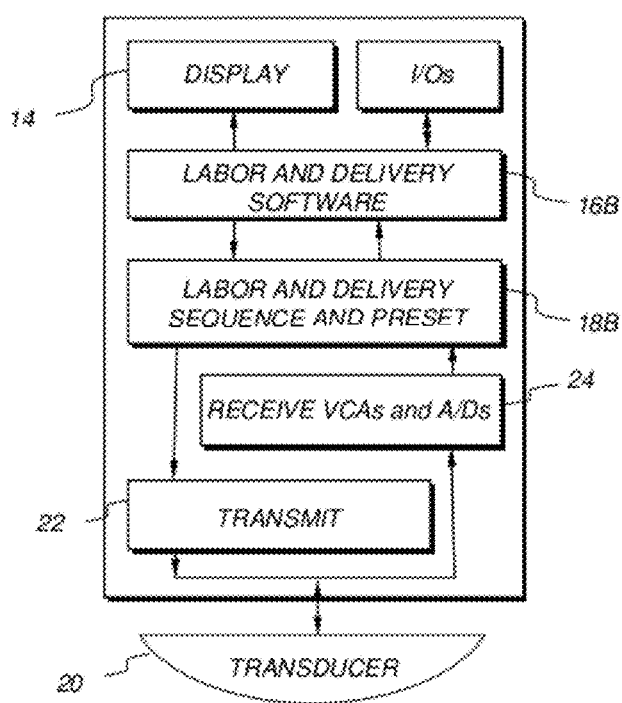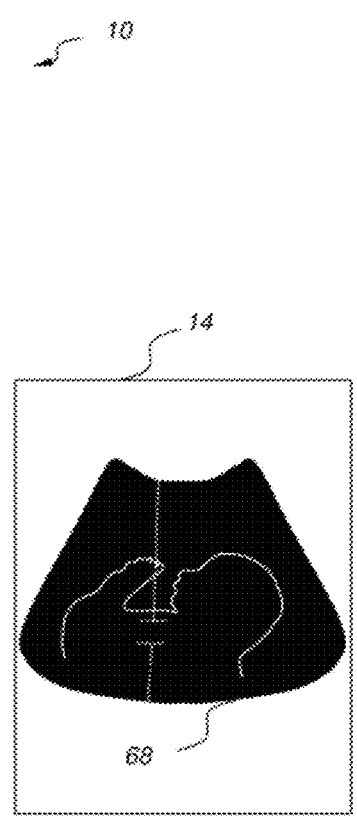
FIG.6A
FIG.6B

HANDHELD ULTRASOUND IMAGING SYSTEMS

REFERENCE TO RELATED APPLICATIONS

This application is a continuation of U.S. patent application Ser. No. 12/188,122 filed 7 Aug. 2008, which claims the benefit under 35 U.S.C. §119 of U.S. patent application No. 60/977,353 filed 3 Oct. 2007, all of which are entitled HANDHELD ULTRASOUND IMAGING SYSTEMS and are hereby incorporated by reference. This application claims the benefit under 35 U.S.C. §120 of U.S. patent application Ser. No. 12/188,122 filed 7 Aug. 2008 and entitled HANDHELD ULTRASOUND IMAGING SYSTEMS.

TECHNICAL FIELD

This invention relates to medical monitoring systems. The invention relates particularly to systems which apply ultrasound to detect physiological features or characteristics of a subject. Embodiments of the invention provide handheld ultrasound imaging devices.

BACKGROUND

Ultrasound imaging systems are used in medicine to explore internal areas of a subject's body. Ultrasonic imaging is non-destructive and versatile and can provide high quality diagnostic images.

A typical medical ultrasound imaging system has a transducer, a custom built electronic controller, and a user interface. The transducer typically comprises an array of at least several regularly-spaced piezoelectric transducer elements. The transducer elements may be arranged in any of several different geometries, depending upon the medical application for which the transducer will be used.

The controller drives the transducer to emit ultrasound signals and collects and processes data from the transducer to provide, store, display and manipulate images. The user interfaces for typical ultrasound imaging systems typically include various input/output devices which allow a user to control the operation of the imaging system. The input/output devices typically comprise at least a control panel, a video display, and a printer.

The electronic controller can send and receive electric signals to and from any of the transducer elements. To create a diagnostic image, the controller transmits electrical excitation signals to the transducer elements. The transducer elements convert the excitation signals into ultrasonic vibrations, which are transmitted into the subject's body. The ultrasonic vibrations typically have frequencies in the range of about 2 MHz to about 12 MHz. The ultrasonic vibrations are scattered and reflected by various structures in the subject's body. Some of the reflected and/or scattered ultrasonic vibrations, which may be called echoes, are received at the transducer. The echoes cause the transducer elements to generate electrical signals. After the excitation signals have been transmitted the controller receives and processes the electric signals from the transducer elements.

The resulting image is displayed in real time on a display. The classic presentation of the display, called B-mode, is a two-dimensional image of a selected cross-section of the patient's body. Modern ultrasound systems also provide flow-imaging modes such as Color Doppler and Pulsed Doppler, which show and can help to quantify blood flow.

Recent miniaturization of electronics has enabled the design of a generation of lighter, portable or handheld ultrasound systems. Ultrasound systems described in the patent literature include the following US patents:

U.S. Pat. No. 5,295,485 to Shinomura et al. describes a handheld ultrasound imaging system that can be adapted to support multi element array transducers and includes a beamformer.

U.S. Pat. No. 5,722,412 to Pflugrath et al., U.S. Pat. No. 5,817,024 to Ogle et al., and U.S. Pat. No. 6,203,498 to Bunce et al. describe handheld ultrasound systems built around a set of ASIC (Application Specific Integrated Circuit) chips. The systems include a transducer array, an ASIC transmit/receive front end, an ASIC that includes digitization and digital beamforming capabilities, an ASIC for signal processing and an ASIC for display processing.

U.S. Pat. Nos. 6,251,073 and 6,569,102 to Imran et al. describe a handheld ultrasound system that can construct an image built from multiple transmit/receive acquisitions that are temporarily stored in a memory. The handheld system has the ability to output a diagnostic image built from multiple transmit/receive acquisitions.

U.S. Pat. Nos. 5,590,658, 6,106,472, and 6,638,226 to Chiang et al. describe a handheld ultrasound system that includes a transducer coupled to a CCD-based analog beamformer and post processing electronics. The system uses a separate back-end to further process and display diagnostic images.

U.S. Pat. No. 7,115,093 to Halmann et al. describes a handheld ultrasound imaging system comprising a detachable scanhead coupled to a traditional beamforming module, that is connected via a USB (Universal Serial Bus) port to a commercially available PDA (Portable Digital Assistant). The PDA performs post processing functions to yield ultrasound images.

The inventors have recognized a need for a handheld ultrasound imaging device that is cost effective and can be configured to operate in multiple different modes to address different application-specific needs.

BRIEF DESCRIPTION OF THE DRAWINGS

Non-limiting example embodiments are illustrated in the accompanying drawings. The embodiments and figures disclosed herein are examples that illustrate ways in which the invention may be implemented. The invention is not limited to the illustrated embodiments.

In FIG. 2A the transducer assembly has elements arranged in a convex array. In FIG. 2B the transducer assembly has elements arranged in a linear array. In FIG. 2C the transducer assembly has elements arranged to provide a phased array.

FIG. 6A is a block diagram of an ultrasound imaging device configured for monitoring labour and delivery in obstetrics applications and FIG. 6B is an example of an image of the type that could be produced by the ultrasound imaging device of FIG. 6A.

DESCRIPTION

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

An example embodiment of the invention provides a handholdable ultrasound imaging device that can be configured to perform a range of specific ultrasound imaging procedures. The device preferably has a form-factor that permits it to be carried in a shirt pocket. The device may provide a simplified user interface for each operational mode so that it can be used by personnel who may not have extensive training The different operational modes may be selected for use in different point of care settings, where a practitioner is interested in looking inside patients' bodies for gathering anatomy information, monitoring vital functions, targeting a particular body structure, observing organ configurations, looking at fetal positions or the like.

The features of the invention described herein may be combined in any suitable combinations with the features described in the commonly-owned US provisional patent applications entitled:
  HAND-HELD ULTRASOUND SYSTEM HAVING STERILE ENCLOSURE (application No. 60/955,327);
  HAND-HELD ULTRASOUND IMAGING DEVICE HAVING RECONFIGURABLE USER INTERFACE (application No. 60/955,328);
  POWER MANAGEMENT IN PORTABLE ULTRASOUND DEVICES (application No. 60/955,329);
  HAND-HELD ULTRASOUND IMAGING DEVICE HAVING REMOVABLE TRANSDUCER ARRAYS (application No. 60/955,325); and
  WIRELESS NETWORK HAVING PORTABLE ULTRASOUND DEVICES (application No. 60/955,331)
all of which are hereby incorporated herein by reference. The features of the invention described herein may also be combined in any suitable combinations with the features described in the commonly-owned US non-provisional patent applications which are filed on the same day as the instant application and entitled:
  HAND-HELD ULTRASOUND SYSTEM HAVING STERILE ENCLOSURE (claiming priority from application No. 60/955,327);
  HAND-HELD ULTRASOUND IMAGING DEVICE HAVING RECONFIGURABLE USER INTERFACE (claiming priority from application No. 60/955,328);
  POWER MANAGEMENT IN PORTABLE ULTRASOUND DEVICES (claiming priority from application No. 60/955,329);
  HAND-HELD ULTRASOUND IMAGING DEVICE HAVING REMOVABLE TRANSDUCER ARRAYS (claiming priority from application No. 60/955,325); and,
  WIRELESS NETWORK HAVING PORTABLE ULTRASOUND DEVICES (claiming priority from application No. 60/955,331)
all of which are hereby incorporated herein by reference.

Figure 1:
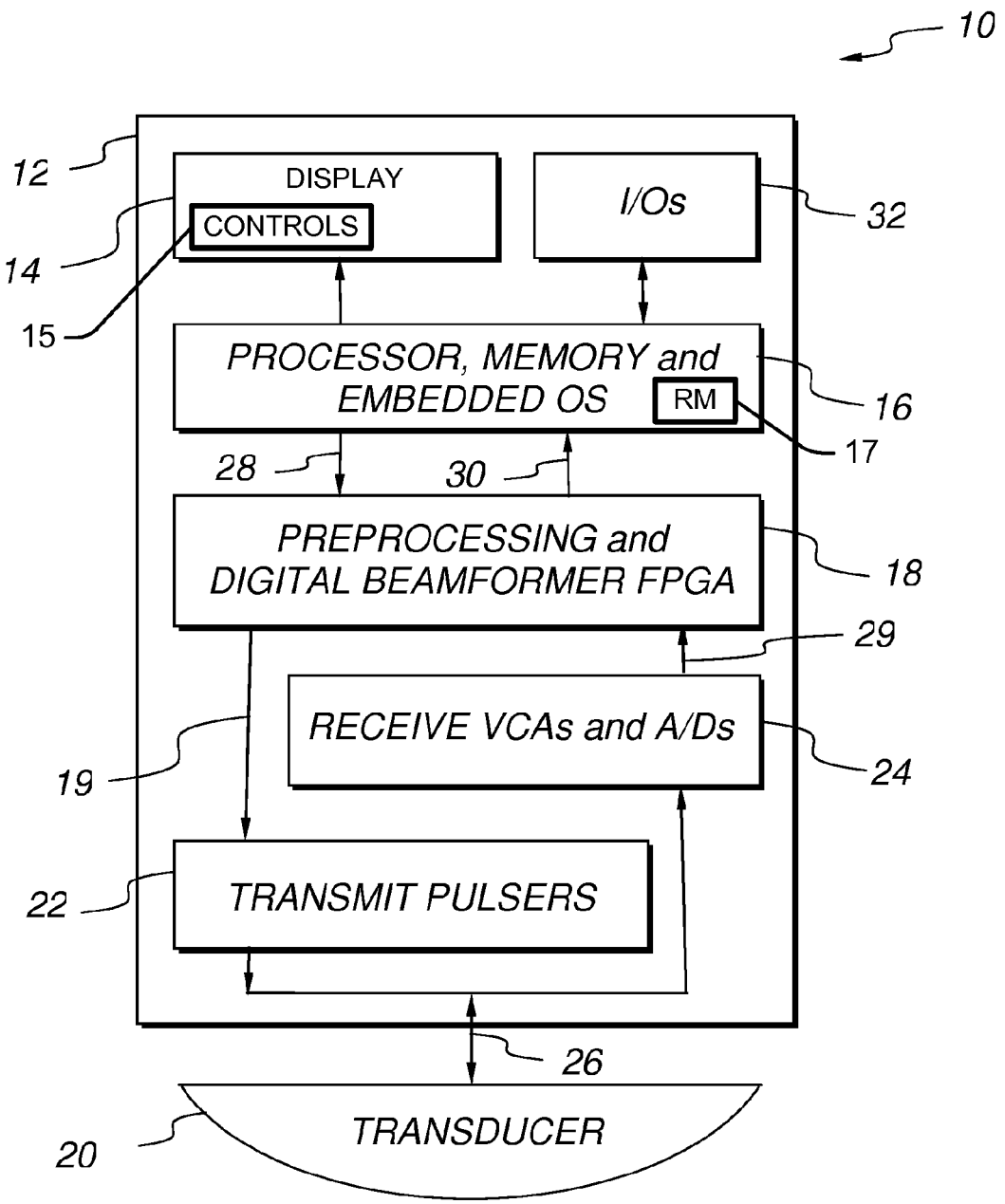
FIG. 1 is a block diagram illustrating major functional components of a ultrasound imaging device according to an embodiment of the invention.

FIG. 1 shows an ultrasound imaging device 10 according to an example embodiment of the invention. Device 10 has a housing 12 containing electronic circuitry which controls transducer elements in a transducer assembly 20 to transmit ultrasound signals into a subject. The electronic circuitry also receives ultrasound signals that have been reflected from within the subject and processes those ultrasound signals to yield an image.

Device 10 comprises a display 14 upon which an image may be displayed, a processor unit 16 which may comprise a data processor, memory and associated operating system, and a configurable signal processing unit 18. Under the control of processor unit 16, signal processing unit 18 may be configured to provide signal processing appropriate to different operational modes.

Some examples of different operational modes are modes tailored to:
  obtaining at least basic information about fetus position prior to and during delivery in labour and delivery rooms;
  monitoring a position of a needle in biopsy line placement and optionally providing a biopsy guide display;
  screening for conditions such as Abdominal Aortic Aneurysm; and,
  the like.

Device 10 optionally includes a stored user manual and/or a stored audio and/or visual user guide that can be played to a user on device 10. The user manual and user guide may explain use of device 10 in the current operational mode.

When device 10 is operating in an operational mode, processor unit 16 interacting with signal processing unit 18 generates control signals 19 which cause transmit pulsers 22 to generate driving signals for transducer elements in transducer assembly 20. The driving signals are delivered to transducer assembly 20 by way of interface 26. The timing, phases, intensities and/or other characteristics of the driving signals may be set to provide ultrasonic signals appropriate to the current operational mode. For example, the timing, phases, intensities and/or other characteristics of the driving signals delivered to transducer assembly 20 may be controlled by signal processing unit 18 (using control signals 19) which may in turn be configured for the current operational mode by processing unit 16 (using appropriate control signals on data path 28).

Transducer assembly 20 has elements which pick up reflected ultrasound signals. These reflected signals are passed through interface 26 to receive signal conditioning stage 24. Signal conditioning stage 24 may include filters, voltage controlled amplifiers, and the like to condition incoming signals. Signal conditioning stage 24 also includes one or more analog to digital converters which digitize the signals picked up by elements of transducer assembly 20 and pass the digitized signals 29 to signal processing unit 18.

Within signal processing unit 18, signals 29 are entirely or partially processed and then passed on data connection 30 to processor unit 16 which displays the resulting image on display 14 or, in the alternative, provides further processing of the signals on data path 30 (i.e. from signal processing unit 18) and then displays the resulting image on display 14.

In some embodiments the signals passed to processor unit 16 by signal processing unit 18 (on data path 30) comprise RF data (e.g. data provided at a rate that is two or more times the frequency of the ultrasound emitted by transducer assembly 20). In such embodiments, processor unit 16 performs further processing to derive image data from the RF data. By way of non-limiting example, processor unit 16 may perform functions such as: frequency analysis of the received signals (by way of a fast Fourier transform (FFT) algorithm, for example); auto-correlation; and the like in addition to or as part of obtaining the image data.

In modes which involve Doppler imaging, signal processing unit 18 may be configured to perform digital wall filtering and/or auto-correlation.

As is apparent from the above, some functions that are required in the signal path for certain operational modes may be performed either by processor unit 16 or by signal processing unit 18. In some cases, performance may be increased by performing functions such as filtering, envelope detection, log compression, auto-correlation in processor unit 16. This may permit additional functions to be provided in signal processing unit 18 in those cases where the capacity of signal processing unit 18 is limited.

In some embodiments, signal processing unit 18 is configured to perform beamforming on at least the signals received from transducer assembly 20. In some embodiments, in addition to beamforming, signal processing unit 18 performs filtering and/or envelope detection on the signals received from transducer assembly 20.

In those embodiments where signal processing unit 18 performs filtering of the signals received from transducer assembly 20, signal processing unit 18 may be configurable to implement digital filters having different filter coefficients for different applications. The filter coefficients may be selected to provide a good signal-to-noise ratio for each specific application (e.g. each specific operational mode). For example, the filter coefficients may be selected to pass signals having frequencies in a band around a frequency at which elements of transducer assembly 20 are driven to emit ultrasound. Reconfiguring signal processing unit 18 may comprise programming interconnects (e.g. signal connections) within a section of a field-programmable gate array (FPGA) that implements one or more digital filters for the received signals.

In those embodiments where signal processing unit 18 performs envelope detection on the signals received from transducer assembly 20, signal processing unit 18 may be configurable to select from among a plurality of different envelope detection algorithms. Reconfiguring signal processing unit 18 may comprise programming interconnects (e.g. signal connections) within a section of an FPGA that implements one or more envelope detectors that act on the received signals.

Input/output interface(s) 32 may be provided to place ultrasound device 10 in data communication with one or more other devices. Input/output interface(s) 32 may comprise one or more wireless interfaces (which may, for example, comprise RF wireless interfaces, infrared wireless interfaces or the like) or other connections such as serial connections, USB connections, parallel connections, or the like. In some embodiments, device 10 has wireless connectivity according to the Bluetooth™ standard or an IEEE 802.11 standard (otherwise known as WIFI).

Figure 2A:
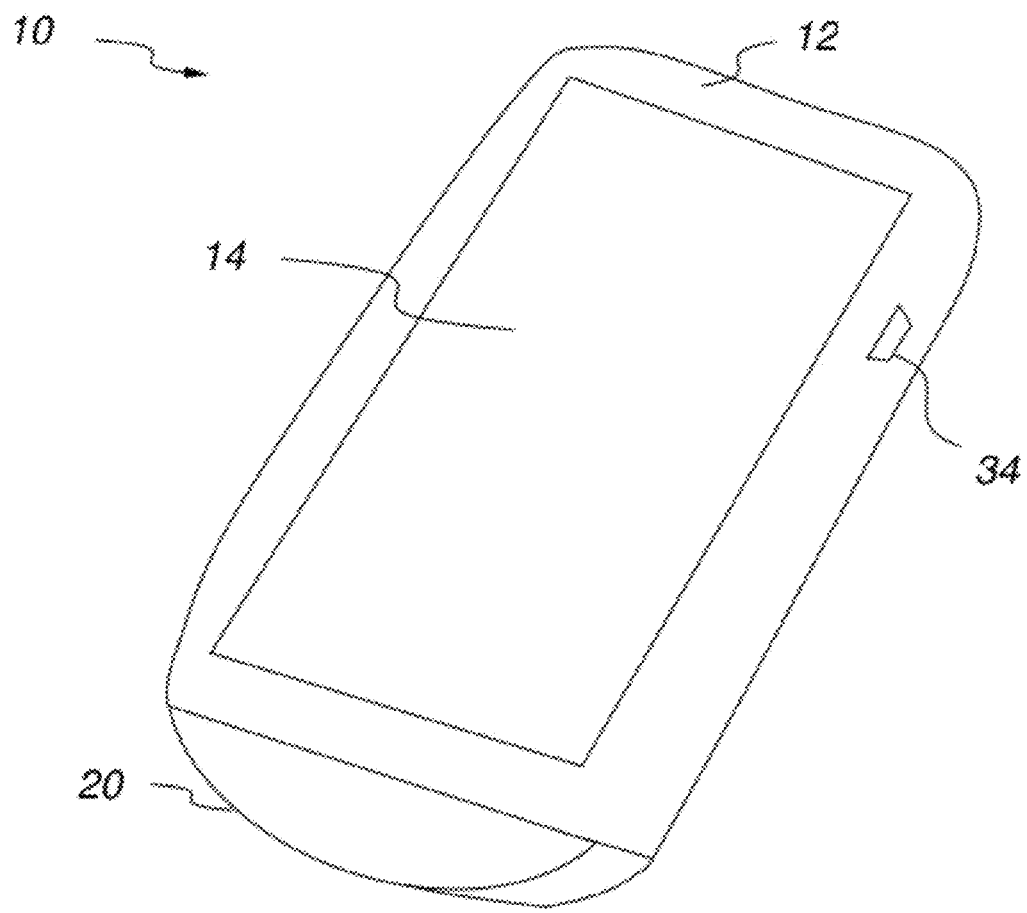
FIGS. 2A, 2B and 2C illustrate an ultrasound imaging device according to an example embodiment of the invention equipped with different transducer assemblies for use in different operational modes.

FIG. 2A shows a handheld ultrasound imaging device 10 according to an example embodiment of the invention. Device 10 has a housing 12 which is suitably small enough to be hand carried, and preferably is small enough to keep in a person's pocket. For example, housing 12 may have dimensions of approximately 10 cm×8 cm×2 cm, and device 10 may weigh less than 10 pounds (i.e. 4.5 kg). A display 14 is provided on housing 12 as are one or more user interface controls 34. Control 34 may, for example, comprise an on/off switch for the purpose of turning device 10 on and shutting device 10 off.

In some embodiments, display 14 comprises a touch-sensitive display and controls for operating device 10 may be provided in the form of touch-sensitive areas on display 14 and/or by way of the capability of device 10 to recognize gestures or other patterns of contact between a user's finger, or a stylus and display 14.

A benefit of the architecture described herein is that it permits the same hardware to be configured in different manners (e.g. different operational modes) so as to provide different specialized imaging functions. For example, ultrasound device 10 may be configured to provide imaging suitable for use in monitoring a fetus prior to and during labour and delivery. The same device 10 may be configured differently to provide imaging that is optimized for guiding a needle, such as a needle for taking a biopsy or some other type of needle into a tissue or other physiological structure of interest. Other operational modes may be provided for some other specific purposes.

Each operational mode may have associated with it a number of different elements. These may include, for example:
 specific configurations of signal processing unit 18 and/or transmit pulsers 22 to generate specific ultrasound signals and to process resulting reflected signals detected at transducer assembly 20 in such a way as to provide ultrasound images appropriate to the operational mode;
 user interface controls which are specific to the operational mode;
 various help functions provided by device 10 which are specific to the operational mode to assist users in properly using device 10 in the operational mode. The help functions include images and videos for display on the display.

The ability to configure a single hardware platform to provide a range of specialized operational modes permits volume manufacture of the platform even in cases where some of the individual operational modes may be very specialized and in relatively low demand. Furthermore, the ability to specialize the device under software control by adding and/or removing and/or repositioning and/or reconfiguring user interface controls 15 on display 14 and/or by changing functions assigned to any interface controls not provided by display 14 permits the device 10 to offer a simplified and highly effective user interface in each of its available specialized operational modes.

In some embodiments, a device 10 can be locked in a selected operational mode. Such a device may be sold at a relatively low cost without disrupting the market for devices 10 configured to perform in other operational modes.

The user interface may be provided as described in co-pending U.S. Patent Application No. 60/955,328 entitled Hand-held Ultrasound Imaging Device Having Reconfigurable User Interface (filed on 10 Aug. 2007) or its counterpart US non-provisional application of the same title (filed on the same date as the instant application) both of which are hereby incorporated herein by reference.

In some cases for different operational modes it is desirable to provide different arrangements of transducer elements in transducer assembly 20. For this purpose, device 10 may be configured to permit the use of interchangeable transducer assemblies 20 that may be removed and replaced with different transducer assemblies suitable for different operational modes. For example, device 10 may be configured as described in U.S. Patent Application No. 60/955,325 entitled Hand-held Ultrasound Imaging Device Having Removable Transducer Arrays (filed on 10 Aug. 2007) or its counterpart US non-provisional application of the same title (filed on the same date as the instant application) both of which are hereby incorporated herein by reference.

In such cases, device 10 may be configured so that it automatically switches between operational modes in response to detecting that a transducer assembly 20 has been changed to a different type of transducer assembly. In the alternative, device 10 can perform a routine to detect the type of connected transducer assembly 20, either on initialization or at some other time and can select an appropriate operational mode based upon information identifying the type of transducer assembly 20 identified in the initialization routine.

Figure 2B:
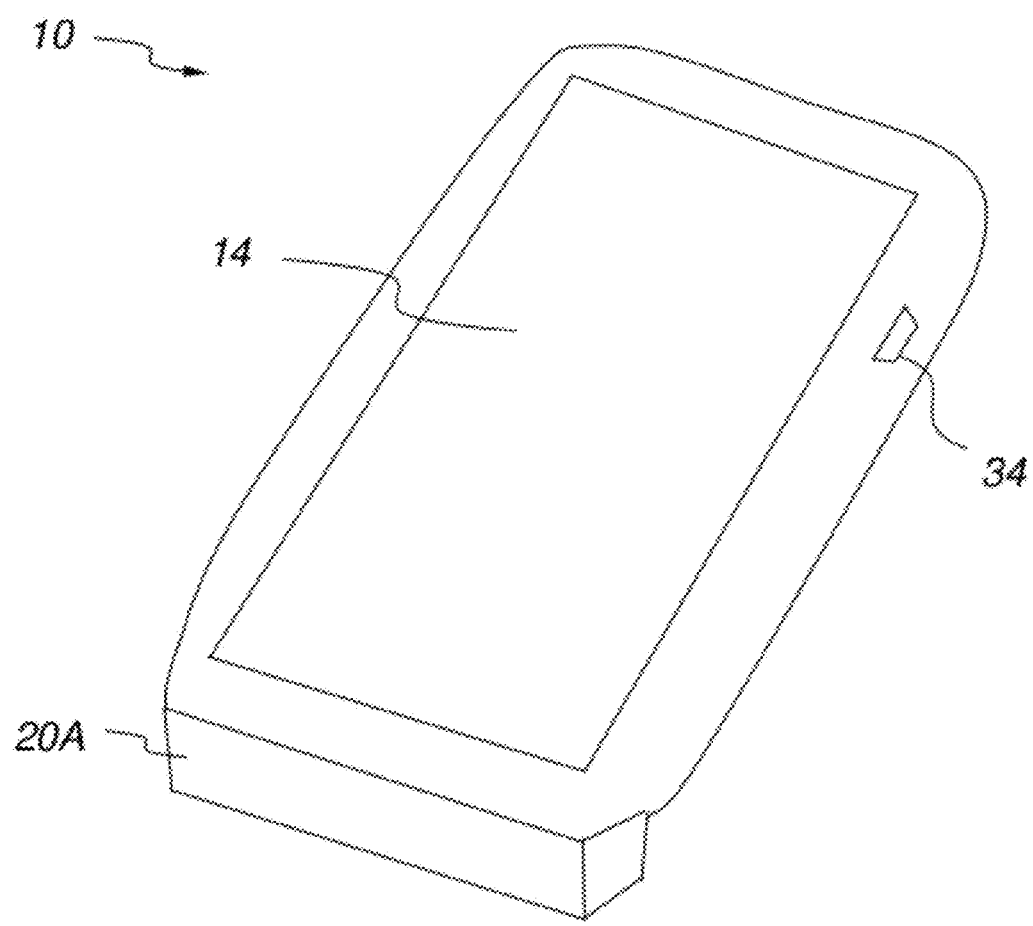
Figure 2C:
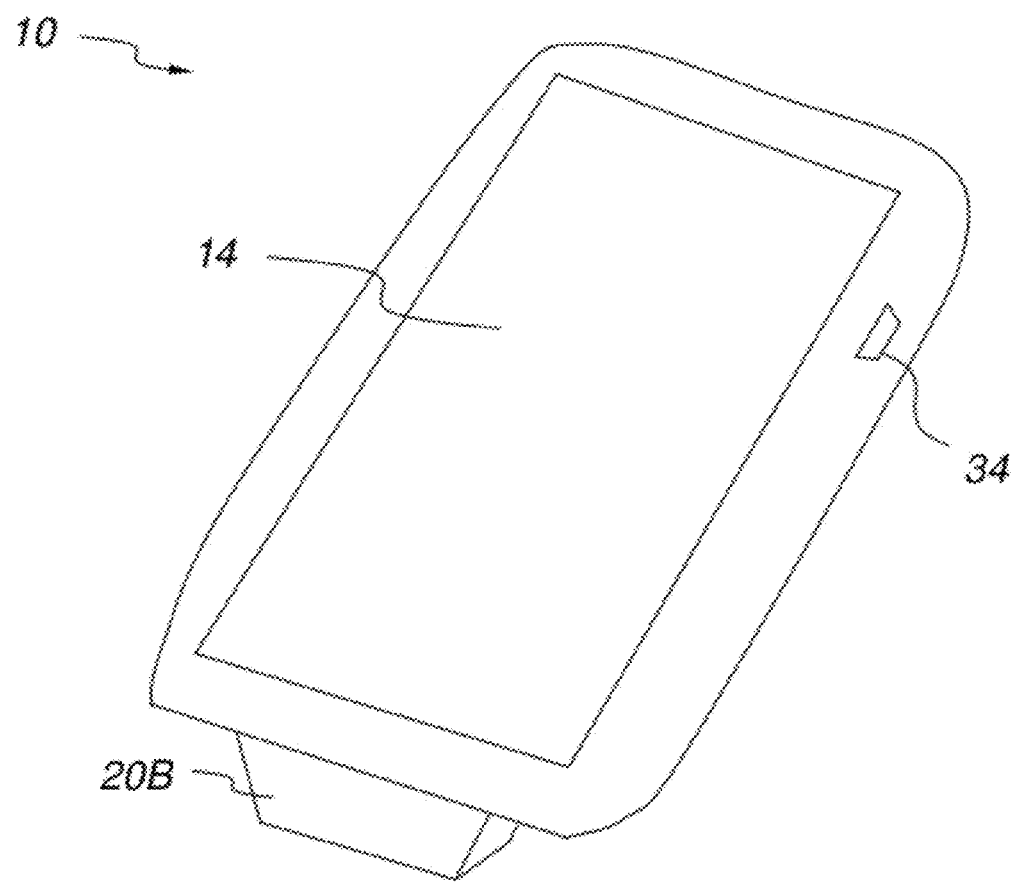

FIGS. 2A, 2B and 2C show, for example, a device 10 to which different transducer assemblies 20, 20A and 20B have been attached respectively. A different operational mode may correspond to each of transducer assemblies 20, 20A and 20B. Device 10 may be switched between these operational modes by selecting and installing the corresponding transducer assembly.

In other embodiments, a device 10 may be switched between operational modes by means of a control provided on a user interface. In still other embodiments, device 10 is intended to offer a single specific operational mode. Device 10 may be upgraded to provide enhanced features or to work according to some different operational mode by uploading new configuration data to device 10 by way of input/output interface(s) 32. In some embodiments, device 10 stores configuration data on a removable medium such as a card, chip, memory stick, memory or the like. In such embodiments it may be possible to upgrade an existing operational mode or add or change to a new operational mode by replacing the removable medium 17 with a removable medium that has configuration data for the new or upgraded operational mode. In some embodiments, device 10 may have configuration data for a number of different operational modes but some of the operational modes may be locked out until a password, digital key, or other authorization code is provided to release the functionality of some of the operational modes.

Figure 3:
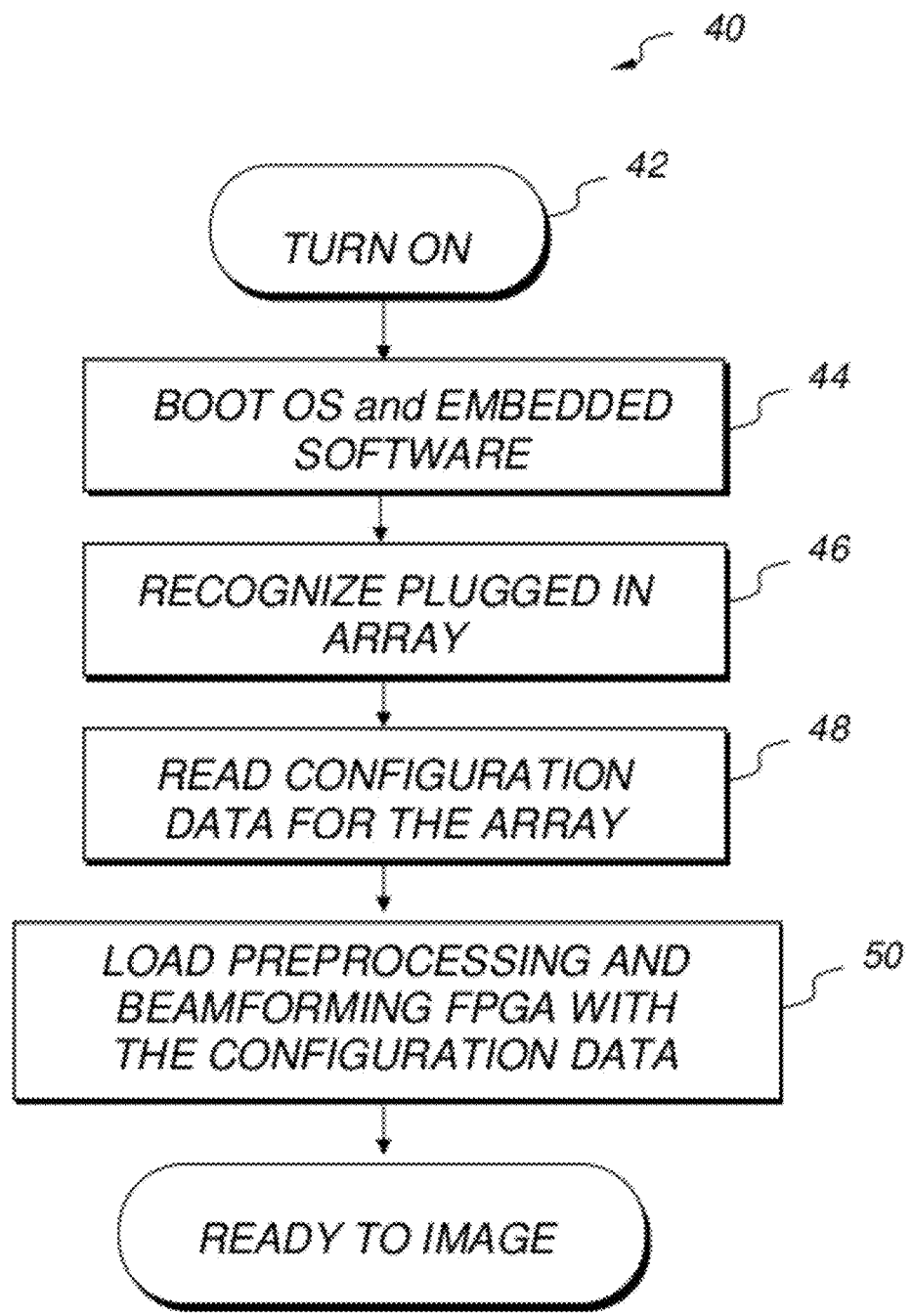
FIG. 3 is a flow chart illustrating a method for initializing an imaging device according to an embodiment of the invention.

FIG. 3 shows a method 40 that may be implemented when a device 10 as described above is turned on. In block 42 the device is turned on. In block 44, device 10 initializes itself by starting to run its operating system and then invoking embedded software which coordinates the overall operation of device 10 (e.g. on a processor of processor unit 16). In block 46, the type of transducer assembly 20 that is connected to device 10 is determined (either by detecting information identifying the transducer assembly 20 or in some embodiments by receiving user input).

In block 48, the configuration data for the operational mode corresponding to the transducer assembly 20 recognized in block 46 is read and, in the illustrated embodiment, signal processing unit 18 is configured according to the configuration data in block 50. The configuration data may additionally specify software to be run on processor unit 16 to support imaging in the corresponding operational mode. In block 50, the transmit and receive circuitry (i.e. transmit pulsers 22 and receive signal processing stage 24) may be shut down and placed in a standby mode waiting for instructions to commence imaging.

Although not specifically shown in FIG. 3, user interface controls and/or user manual information associated with the operational mode may also be loaded by processor unit 16 as a part of method 40 or otherwise.

Imaging may commence automatically upon device 10 detecting that transducer assembly 20 is in contact with a subject or, in the alternative, may be invoked by means of a suitable user interface control.

Figure 4:
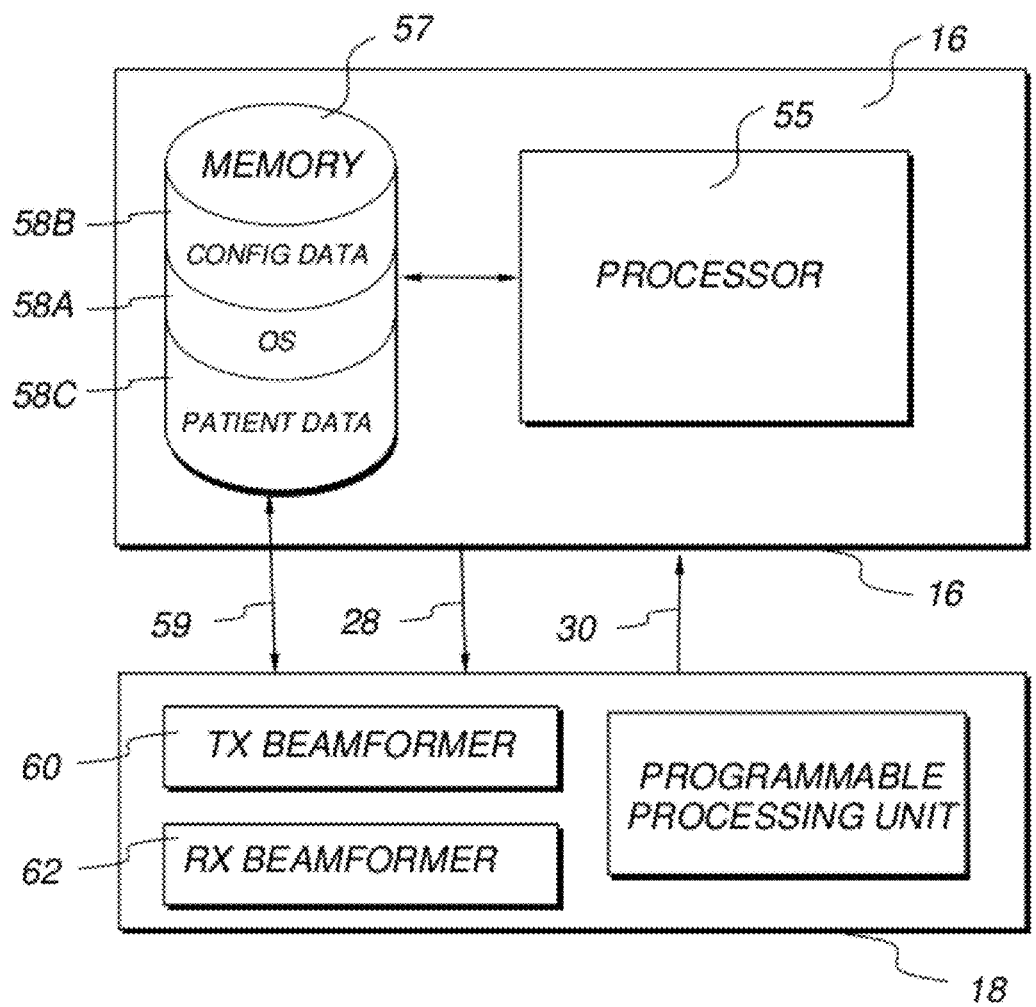
FIG. 4 is a more detailed view illustrating features of a processor unit and a signal processing unit in an example embodiment.

FIG. 4 shows, in more detail, processor unit 16 and signal processing unit 18 according to a particular embodiment. Processor unit 16 comprises one or more suitable data processor(s) 55—a single data processor 55 is shown in the illustrated embodiment. Data processor 55 may, for example, comprise a suitable microprocessor, digital signal processor (DSP), image processor, or the like. In an example embodiment, data processor 55 comprises a BlackFin™ digital signal processor available from Analog Devices, Inc. of Norwood Mass.

Processor 55 is capable of executing software instructions which may be stored in memory 57 accessible to processor 55 or which may be otherwise accessible to processor 55. In the illustrated embodiment, memory 57 contains an operating system 58A and configuration data 58B for one or more operational modes. Memory 57 may also have capacity to store patient data 58C (e.g. images, information identifying patients, or the like).

Processor 55 can cause configuration data (e.g. for a particular operational mode and/or for a particular type of transducer array 20) to be delivered to signal processing unit 18 by data path 28 or directly from a memory 57 to signal processing unit 18 by way of a suitable bus (e.g. bus 59) connected to deliver the configuration data from memory 57 to signal processing unit 18. Such configuration data may comprise all or a part of configuration data 58B stored in memory 57. The configuration data may cause suitable interconnects (e.g. signal processing paths) to be created within signal processing unit 18 for the purpose of generating suitable transmitted ultrasound signals and processing received ultrasound signals in such a manner as to produce an image appropriate for the current operational mode.

In the embodiment illustrated in FIG. 4, signal processing unit 18 is configured by configuration data delivered by way of data path 28 to provide a transmit beamformer 60 and a receive beamformer 62. Depending upon the operational mode, transmit beamformer 60 and receive beamformer 62 may comprise different numbers of channels and may be configured in different ways to provide different characteristics of the transmitted ultrasound signal as well as to derive different information from received ultrasound signals.

Processor unit 16 may be configured to synchronize the transmission and reception of ultrasound signals by transducer assembly 20. In such embodiments, synchronization signals may be provided by way of data path 28.

When a received ultrasound signal is passed to signal processing unit 18, the received signal is processed by way of receive beamformer 62 and the resulting data is passed to processor unit 16 by way of data connection 30. Processor 55 processes the data that it receives in a manner specified by the configuration data 58B associated with the current operational mode and displays the resulting data on display 14 in the form of a suitable display. Processor 55 may optionally also store the image data in memory 57 and/or transmit the image data to a network or other device by way of input/output interface(s) 32.

In some embodiments, signal processing unit 18 comprises a field programmable gate array (FPGA) that is connected to a memory 57 by a bus 59. Memory 57 may store configuration data 58B. Such configuration data 58B may comprise configuration data associated with one or more operational modes. By way of non-limiting example, the configuration data associated with each operational mode may comprise information specifying one or more of:

transmit beamforming parameters;
receive beamforming parameters;
filtering parameters;
envelope detection parameters;
etc.

All configuration data 58B may be stored in memory 57. Memory 57 may, for example, comprise a flash memory or the like. Providing a single memory 57 that contains all configuration data 58B simplifies construction and potentially reduces power consumption. Processor unit 16 may control, directly or indirectly, what portion of configuration data 58B is loaded from memory 57 into signal processing unit 18. The portion of configuration data 58B loaded into signal processing unit 18 may be associated with a particular operational mode.

Some embodiments provide the option of configuring signal processing unit 18 differently for each line of an ultrasound image. In some such embodiments, configuration data for all lines of the ultrasound image may be stored in memory 57 and retrieved by way of bus 59 (or data connection 28) on an as-needed basis. For example, signal processing unit 18 may comprise a buffer that holds configuration data for a current ultrasound image line and also has space to receive configuration data for one or more subsequent ultrasound image lines. The configuration data for the subsequent ultrasound image lines may be read into the buffer from memory 57 while the current ultrasound image line is being processed according to configuration data in the buffer. To facilitate such operation, the buffer may be set up as a circular buffer or 'ping-pong' buffer, for example.

Some or all of the configuration data 58B stored in memory 57 may be generated by processor 55 executing suitable software instructions. For example, processor 55 may execute software for calculating filtering coefficients and/or beamforming coefficients for a particular operational mode. User controls may be provided so that a user can define features of the operational mode. The resulting coefficients may then be saved into memory 57 so that they are available to be loaded for configuration of signal processing unit 18 when the user-defined operational mode is invoked.

Figure 5A:
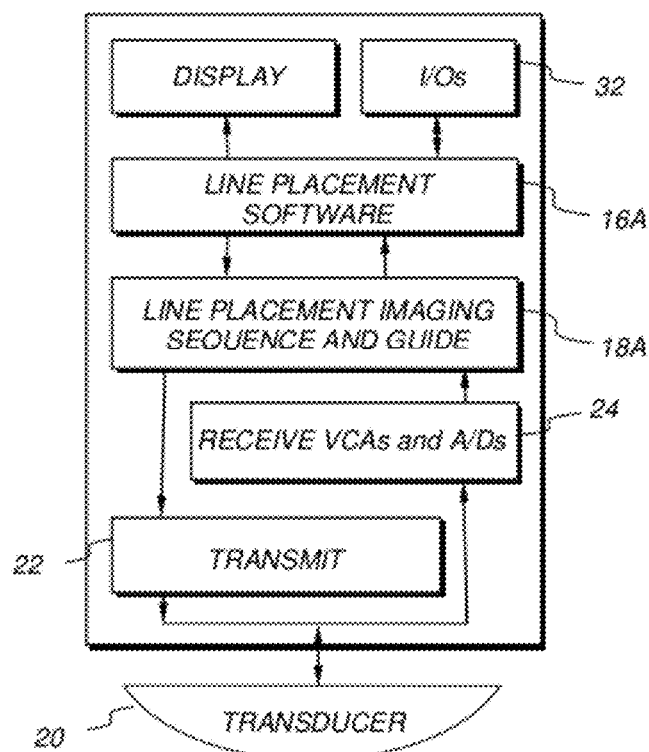
FIG. 5A is a block diagram illustrating an ultrasound imaging device configured for line placement and FIG. 5B is an example of an image that could be generated by the ultrasound imaging device of FIG. 5A.
Figure 5B:
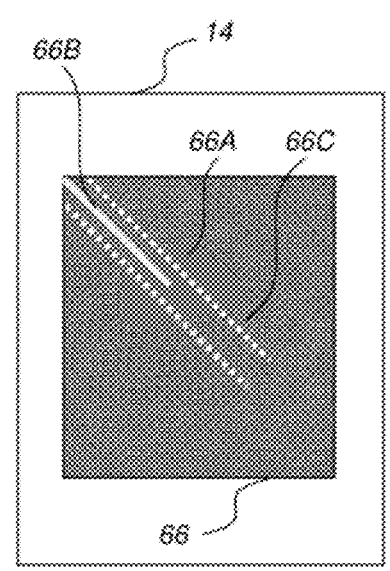

FIG. 5A shows an example of a device 10 which has been configured to provide a line placement operational mode and FIG. 5B shows an example of a resulting image 66 when device 10 is so configured. In the illustrated embodiment, line placement software executes on processor unit 16A and signal processing unit 18A is configured in such a manner as to provide line placement imaging sequence and guide functions. In this operational mode, signal processing unit 18A may be configured with beamforming coefficients that result in enhanced visibility in an image 66 of a needle 66B or the like (FIG. 5B) being inserted into a subject.

FIG. 5B shows an example of an image 66 which could be provided on display 14 during operation of device 10 when it is in the line placement operational mode of FIG. 5A. Image 66 includes depictions 66A of various anatomical structures in the subject, an image of a needle or probe 66B, and generated guide lines 66C which indicate a desired placement of the needle or probe. Parameters used to generate guidelines 66C may be specified in configuration data and/or in software executing on processor unit 16.

FIG. 6A illustrate a device 10 configured to operate in a labour and delivery operational mode which is intended for monitoring the labour or pregnant women and the delivery of babies in obstetric applications and FIG. 6B shows an example of a resulting image 68 which may be provided on display 14 when device 10 is so configured. In this embodiment, processor unit 16B is configured to execute labour and delivery software and signal processing unit 18B is configured to generate ultrasound signals and process detected ultrasound signals in ways suitable for providing good quality images of a fetus in utero and/or in the birth canal.

A device 10 may usefully include features as described in co-pending U.S. Application No. 60/955,329 entitled Power Management in Portable Ultrasound Devices (filed on 10 Aug. 2007) or its counterpart US non-provisional application of the same title (filed on the same date as the instant application) both of which are hereby incorporated herein by reference. These applications describe the use of configuration data to place an ultrasound device in different operational modes as well as to use configuration data to place the ultrasound device in various power consumption modes.

As discussed above, signal processing unit 18 may comprise an FPGA. Advantageously, the same FPGA may be configured to both generate control signals for transmit pulsers 22 and to provide processing of detected signals received from elements of transducer assembly 20. Providing both of these functions in a single FPGA is advantageous because it reduces the width of the signal path required between processor unit 16 and signal processing unit 18.

Example embodiments of the invention may be made from readily-available off the shelf components as contrasted with custom circuitry such as complicated application specific integrated circuits (ASICS) which are required to provide specialized functions in other devices.

Where a component (e.g. a processor, circuit, beamformer, signal conditioner, filter, control, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention. The embodiments described above and depicted in the Figures are examples only. Features of those embodiments may be combined in ways other than those expressly set out herein.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:
1. A hand-holdable ultrasound system comprising:
   a detachable transducer assembly comprising a plurality of transducer elements, the detachable transducer assembly interchangeable with one or more other detachable transducer assemblies, the detachable transducer assembly and the one or more other detachable transducer assemblies are suitable for ultrasound imaging in a respective one of a plurality of different operational modes of the ultrasound system, the detachable transducer assembly not attached to or part of a transducer probe, and the detachable transducer assembly attaches directly to the hand-holdable ultrasound system and not through a transducer probe;
   a driving circuit operable to deliver driving signals to excite the transducer elements of the transducer assembly to emit ultrasound signals, the driving circuit comprising a plurality of transmit pulsers;

a receive circuit operable to receive reflected ultrasound signals detected at the transducer assembly and to condition the received reflected ultrasound signals to yield conditioned signals, the receive circuit comprising one or more analog to digital converters arranged to digitize the received reflected ultrasound signals;

a configurable signal processing unit connected to receive the digitized conditioned signals and to process the conditioned signals, the configurable signal processing unit comprising
   a field programmable gate array;
   a processor unit comprising one or more data processors and
   a memory, the memory storing software instructions for execution by the one or more processors and pre-stored with a plurality of sets of configuration data, each of the plurality of sets of configuration data corresponding to a different one of the operational modes of the plurality of operational modes;

a display operable to display an image based at least in part on the reflected ultrasound signals detected at the transducer assembly; and one or more user interface controls for providing user input to the hand-holdable ultrasound system;

wherein the software instructions are configured to cause the one or more data processors to: identify a type of the detachable transducer assembly; based on the identified type of the detachable transducer assembly, select a respective one of the plurality of operational modes corresponding to the identified type of the detachable transducer assembly for which the ultrasound system will be configured; and configure each of: the signal processing unit, the transmit circuit, the processor and the user interface controls according to the one of the sets of configuration data corresponding to the selected operational mode; wherein:

the sets of configuration data for different ones of the plurality of operational modes are configured to configure the signal processing unit to implement digital filters having different filter coefficients to provide filtering of the conditioned reflected ultrasound signals received from the transducer assembly;

the set of configuration data for at least one of the operational modes is configured to configure the field programmable gate array to both generate control signals for the transmit circuit and to provide processing of detected signals received from elements of the transducer assembly;

the set of configuration data for at least one of the operational modes is configured to identify software to be run on the processor unit to support imaging in the corresponding operational mode, the software configured to cause the processor unit to perform one or more of: filtering, envelope detection, log compression, and autocorrelation;

the set of configuration data for at least one of the operational modes is configured to configure the signal processor unit to pass RF data to the processor unit at a rate that is two or more times a frequency of the ultrasound signals and to configure the processor unit to perform further processing to derive image data from the RF data by one or more of: fast Fourier transform of the RF data and auto-correlation; or the set of configuration data for at least one of the operational modes is configured to configure the signal processor unit to provide a transmit beamformer and a receive beamformer, the transmit beamformer and receive beamformer having different numbers of channels;

the plurality of operational modes comprises a line placement operational mode, one of the sets of configuration data comprises line placement configuration data, and the ultrasound system is configured according to the line placement configuration data to provide imaging that is optimized for guiding a needle into a tissue or another physiological structure, the line placement configuration data specifying line placement software to be executed by the processor unit and configured to configure the signal processing unit with beamforming coefficients, one or both of the line placement configuration data and the line placement software comprising parameters for generating guidelines on the display to indicate a desired placement of athe needle.

2. The hand-holdable ultrasound system according to claim 1 wherein the hand-holdable ultrasound system weighs less than 10 pounds and has transverse and longitudinal dimensions less than about 15 centimeters and a width less than about 5 centimeters.

3. The hand-holdable ultrasound system according to claim 1 wherein each of the sets of configuration data provides:
   a specific configuration of the signal processing unit and the transmit pulsers to generate specific ultrasound signals and to process resulting reflected signals detected at the transducer assembly to provide ultrasound images appropriate to the corresponding operational mode;
   user interface controls which are specific to the corresponding operational mode; and help functions specific to the corresponding operational mode to assist users in properly using the ultrasound system in the corresponding operational mode, the help functions comprising images and videos for display on the display.

4. The hand-holdable ultrasound system according to claim 1 wherein the ultrasound system comprises a set of transducer assemblies and the detachable transducer assembly is one of the set of transducer assemblies, the set of transducer assemblies comprising a first transducer assembly comprising a convex array of transducer elements, a second transducer assembly comprising a linear array of transducer elements and a third transducer assembly comprising a phased array of transducer elements.

5. The hand-holdable ultrasound system according to claim 1 comprising one or more input/output interfaces for receiving the configuration data, prior to storing the configuration data in the memory, into the hand-holdable ultrasound system wherein the one or more input/output interfaces comprise at least one of: an interface to a removable memory medium; a wireless communication interface; a serial data interface; a parallel data interface; and a universal serial bus interface.

6. The hand-holdable ultrasound system according to claim 1 wherein the memory comprises a removable memory medium and the configuration data is stored on the removable memory medium.

7. The hand-holdable ultrasound system according to claim 1 wherein, for each of the plurality of operational modes the one or more user interface controls comprise a user interface control configured for providing a help request to the hand-holdable ultrasound system and wherein the processor unit is configured to respond to the help request in a manner which is specific to a current one of the plurality of operational modes.

8. The hand-holdable ultrasound system according to claim 1 wherein the display comprises one or more touch-sensitive user interface controls for providing user input to the hand-holdable ultrasound system and the processor unit is configured to add, remove, reposition and reconfigure the user interface controls on the display under software control on switching among the operational modes.

9. The hand-holdable ultrasound system according to claim 1 wherein, for at least a first one of the plurality of operational modes, the processor unit is configured to provide configuration data to the signal processing unit to configure the signal processing unit to provide different signal processing operations for different lines of an ultrasound image.

10. The hand-holdable ultrasound system according to claim 9 wherein for the first one of the operational modes configuration data for all lines of an ultrasound image is stored in the memory and the signal processing unit is configured to retrieve the configuration data for the lines of the ultrasound image on an as-needed basis.

11. The hand-holdable ultrasound system according to claim 10 wherein the set of configuration data for the first one of the operational modes is configured to configure the signal processing unit to provide a buffer that holds configuration data for a current ultrasound image line wherein the buffer also has space to hold configuration data for one or more subsequent ultrasound image lines.

12. The hand-holdable ultrasound system according to claim 11 wherein the set of configuration data for the first one of the operational modes is configured to configure the signal processing unit to read configuration data for subsequent ultrasound image lines into the buffer from the memory while a current ultrasound image line is being processed according to the configuration data for the current ultrasound image line that is in the buffer.

13. The hand-holdable ultrasound system according to claim 11 wherein the buffer comprises a circular buffer.

14. The hand-holdable ultrasound system according to claim 1 wherein for each of the plurality of operational modes, timing, phases, and intensities of the driving signals delivered to the transducer assembly are controlled by the signal processing unit which has been configured for the current operational mode by the processor unit.

15. The hand-holdable ultrasound system according to claim 1 wherein for at least one of the operational modes the signal processing unit is configured to perform envelope detection on the signals received from the transducer assembly.

16. The hand-holdable ultrasound system according to claim 15 wherein the signal processing unit is configurable to provide an envelope detection algorithm from among a plurality of different envelope detection algorithms by programming interconnects within a section of the field programmable gate array that implements one or more envelope detectors arranged to act on the received signals.

17. The hand-holdable ultrasound system according to claim 1 wherein the ultrasound system is locked in the selected one of the plurality of operational modes.

18. The hand-holdable ultrasound system according to claim 1 wherein the processor unit is configured to synchronize the transmission and reception of ultrasound signals by the transducer assembly by generating synchronization signals and providing the synchronization signals to the signal processing unit.

19. The hand-holdable ultrasound system according to claim 1 wherein the configuration data associated with each of the plurality of operational modes comprises information specifying: transmit beamforming parameters; receive beamforming parameters; filtering parameters; and envelope detection parameters.

20. The hand-holdable ultrasound system according to claim 1 wherein the plurality of operational modes includes a user-defined operational mode and the user interface controls comprise user controls configured to permit a user to define features of the user-defined operational mode.

* * * * *